United States Patent [19]
Fischer et al.

[11] Patent Number: 5,900,507
[45] Date of Patent: May 4, 1999

[54] PROCESS FOR THE PREPARATION OF 1-AMINO-1-METHYL-3(4)-AMINOMETHYL CYCLOHEXANE

[75] Inventors: Konrad Fischer, Odenthal; Oswald Wilmes, Köln; Dieter Arlt, Lemgo; Carl Casser, Köln, all of Germany; Peter Maas, Puth, Netherlands; Pierre Woestenborghs, Dilsen, Belgium; Theo Van Der Knaap, Grevenbicht; Raf Reintjens, Schimmert, both of Netherlands

[73] Assignee: Bayer Aktiengesellschaft, Leverkusen, Germany

[21] Appl. No.: 09/038,331

[22] Filed: Mar. 11, 1998

[30] Foreign Application Priority Data

Mar. 20, 1997 [DE] Germany ............... 197 11 548

[51] Int. Cl.$^6$ .................................. C07C 209/08
[52] U.S. Cl. ................ 564/217; 564/126; 564/448
[58] Field of Search .................. 564/448, 444, 564/461, 462, 217, 126

[56] References Cited

U.S. PATENT DOCUMENTS 5,449,811  9/1995  Arlt ............................. 558/431

Primary Examiner—Brian M. Burn
Attorney, Agent, or Firm—Joseph C. Gil; Thomas W. Roy

[57] ABSTRACT

The present invention relates to a process for the preparation of 1-amino-1-methyl-3(4)-aminomethyl cyclohexane (AMCA) by a) catalytically hydrogenating 1-formamido-1-methyl-3(4)-cyano cyclohexane (FMC) in a first reaction stage to form 1-formamido-1-methyl-3(4)-aminomethyl cyclohexane (FMA), 1-amino-1-methyl-3(4)-formamidomethyl cyclohexane (AMF), 1-formamido-1-methyl-3(4)-formamidomethyl cyclohexane (FMF) and/or AMCA, and b) reacting FMA, AMF and/or FMF in a second reaction stage with an alkaline compound to from AMCA and a formic acid derivative, and c) separating the reaction mixture obtained in step b) into components by fractional distillation and/or by crystallization and filtration.

The present invention is also relates to carrying the hydrogenation reaction of step a) in the presence of a formulating agent to form 1-formamido-1-methyl-3(4)-formamidomethyl cyclohexane (FMF).

Finally, the present invention relates to the intermediate products 1-formamido-1-methyl-3(4)-aminomethyl cyclohexane (FMA) and 1-formamido-1-methyl-3(4)-formamidomethyl cyclohexane (FMF).

11 Claims, No Drawings

PROCESS FOR THE PREPARATION OF 1-AMINO-1-METHYL-3(4)-AMINOMETHYL CYCLOHEXANE

BACKGROUND OF THE INVENTION

1. Field of the Invention

The present invention relates to a process for the production of 1-amino-1-methyl-3(4)-aminomethylcyclohexane (AMCA), the precursor for the production of 1-isocyanato-1-methyl-3(4)-isocyanatomethylcyclo-hexane (IMCI).

2. Description of the Prior Art

DE-A 4,401,929 describes a process for the preparation of 1-amino-1-methyl-3(4)-aminomethyl cyclohexane (AMCA) that may be illustrated by the following reaction scheme:

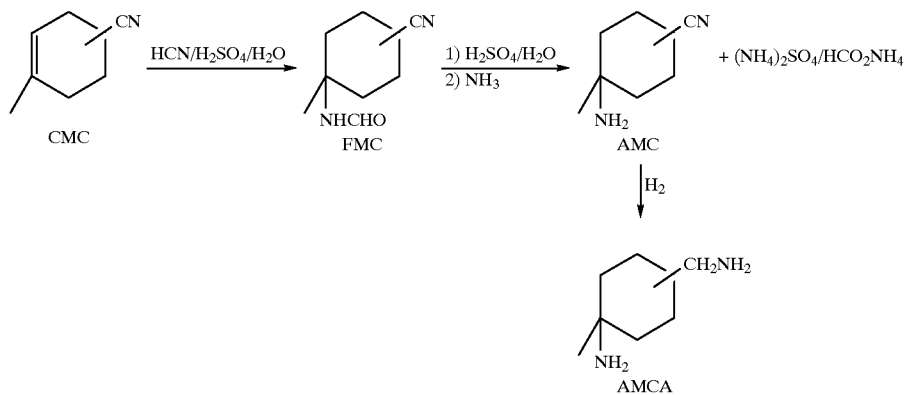

According to the reaction mechanism, 4(5)-cyano-1-methyl cyclohexene (CMC) is reacted with hydrocyanic acid in the presence of sulphuric acid to give 1-formamido-1-methyl-3(4)-cyano cyclohexane (FMC), which can be extracted from the acidic aqueous phase with suitable water-immiscible solvents after excess hydrocyanic acid has been removed by distillation and the reaction mixture has been diluted with water. Another known variant (see DE-A 4,401, 929) for isolating FMC from the aqueous reaction mixture, which arises in accordance with the Ritter reaction, is to neutralize the latter acid mixture with ammonia, optionally after diluting with water, such that the mixture contains about 20 to 70 wt. % of ammonium sulphate, followed by solvent extraction of the FMC which is present in the mixture. In this embodiment of isolating FMC a considerable quantity of ammonium salts is formed because of the neutralization of the sulphuric acid used in the Ritter reaction. However, this is an important process because the extraction is particularly complete even using small quantities of extracting agent, which reduces the energy requirement for further working up. In a further reaction step, the 1-formamido-1-methyl-3(4)-cyano cyclohexane (FMC) is then hydrolysed in the acid aqueous medium to give 1-amino-1-methyl-3(4)-cyano cyclohexane (AMC).

A further process variant of DE-A 4,401,929 is to hydrolyze the 1-formamido-1-methyl-3(4)-cyano cyclohexane (FMC), without prior isolation, using the sulphuric acid present in the Ritter reaction mixture.

In all of the process variants described in DE-A 4,401,929 the 1-formamido-1-methyl-3(4)-cyano cyclohexane obtained following hydrolysis is present in an acidic aqueous solution. The isolation of the 1-amino-1-methyl-3(4)-cyano cyclohexane (AMC) by extraction, which follows in the process, can only be carried out from an alkaline solution if it is to be successful industrially. The result of converting the acidic solution to an aqueous solution is that salts are formed as by-products, which must be used or disposed of. The resulting 1-amino-1-methyl-3(4)-cyano cyclohexane (AMC), optionally after separation of the extracting agent by distillation in a known manner, is then hydrogenated catalytically to give 1-amino-1-methyl-3(4)-aminomethyl cyclohexane (AMCA).

The conversion of the acidic aqueous solution of 1-amino-1-methyl-3(4)-cyano cyclohexane to a basic solution is carried out with ammonia in the German publication, which results in the formation of ammonium sulphate and ammonium formate as by-products. It is proposed to thermolytically cleave the ammonium sulphate to form sulphur dioxide, which can be recycled to produce sulphuric acid.

Because it is necessary to concentrate the aqueous ammonium sulphate solution before it can be cleaved, this treatment of the by-product salts results in considerable distillation costs.

Treatment of the salt solution for the purpose of recycling ammonium sulphate also results in considerable costs because the ammonium sulphate solution obtained has a chemical oxygen demand (COD) of 10 g per liter even after the extracting agent contained in the salt solution has been removed by distillation and the formate has been removed.

In the catalytic hydrogenation of 1-amino-1-methyl-3(4)-cyano cyclohexane (AMC) to 1-amino-1-methyl-3(4)-aminomethyl cyclohexane (AMCA), which is disclosed in the German publication, intramolecular cyclization and intermolecular dimerization processes result in by-products I, II, III, IV and V.

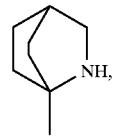

I

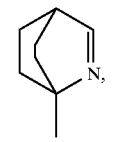

II

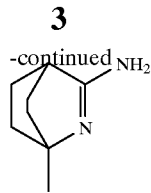

III

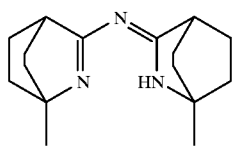

IV

V compound having molar mass: 263
(= AMCA + AMC —— NH₃)

These by-products are present in an amount of approximately 20%. In other words there is a loss of selectivity of approximately 20%.

It is an object of the present invention to provide a process for the preparation of 1-amino-1-methyl-3(4)-aminomethyl cyclohexane (AMCA), which has a markedly higher total selectivity (based on the 4(5)-cyano-1-methyl cyclohexene (CMC) starting material) and in which the ammonium sulphate-containing effluent, which is obtained as an unavoidable by-product, can be worked up economically to give recyclable ammonium sulphate.

This object can be achieved with the process according to the present invention, which is described hereinafter.

SUMMARY OF THE INVENTION

The present invention relates to a process for the preparation of 1-amino-1-methyl-3(4)-aminomethyl cyclohexane (AMCA) by a) catalytically hydrogenating 1-formamido-1-methyl-3(4)-cyano cyclohexane (FMC) in a first reaction stage to form 1-formamido-1-methyl-3(4)-aminomethyl cyclohexane (FMA), 1-amino-1-methyl-3(4)-formamidomethyl cyclohexane (AMF), 1-formamido-1-methyl-3(4)-formamidomethyl cyclohexane (FMF) and/or AMCA, and b) reacting FMA, AMF and/or FMF in a second reaction stage with an alkaline compound to from AMCA and a formic acid derivative, and c) separating the reaction mixture obtained in step b) into components by fractional distillation and/or by crystallization and filtration.

The present invention is also relates to carrying the hydrogenation reaction of step a) in the presence of a formulating agent to form 1-formamido-1-methyl-3(4)-formamidomethyl cyclohexane (FMF).

Finally, the present invention relates to the intermediate products 1-formamido-1-methyl-3(4)-aminomethyl cyclohexane (FMA) and 1-formamido-1-methyl-3(4)-formamidomethyl cyclohexane (FMF).

DETAILED DESCRIPTION OF THE INVENTION

The starting material for the present invention, 1-formamido-1-methyl-3(4)-cyano cyclohexane (FMC), may be formed in known manner, e.g., by the reaction of 4(5)-cyano-1-methyl cyclohexene (CMC) with hydrocyanic acid in the presence of sulphuric acid and subsequent extraction with suitable solvents from the reaction solution after it has been diluted with water or neutralized with ammonia.

After extraction FMC is hydrogenated catalytically, optionally after separating the extracting agent by distillation. The 1-formamido-1-methyl-3(4)-aminomethyl cyclohexane (FMA) or the 1-amino-1-methyl-3(4)-formamidomethyl cyclohexane (AMF) obtained as a result of intramolecular equilibration or the 1-formamido-1-methyl-3(4)-formamidomethyl cyclohexane (FMF) and AMCA obtained as a result of intermolecular equilibration are new intermediate products.

If the hydrogenation is carried out in the presence of a formulating agent, 1-formamido-1-methyl-3(4)-formamidomethyl cyclohexane (FMF) is obtained as a new intermediate product. The intermediate products FMA, AMF and FMF are then reacted with alkaline compounds to provide 1-amino-1-methyl-3(4)-aminomethyl cyclohexane (AMCA) and a formic acid derivative.

The processes according to the invention are illustrated by the following reaction scheme:

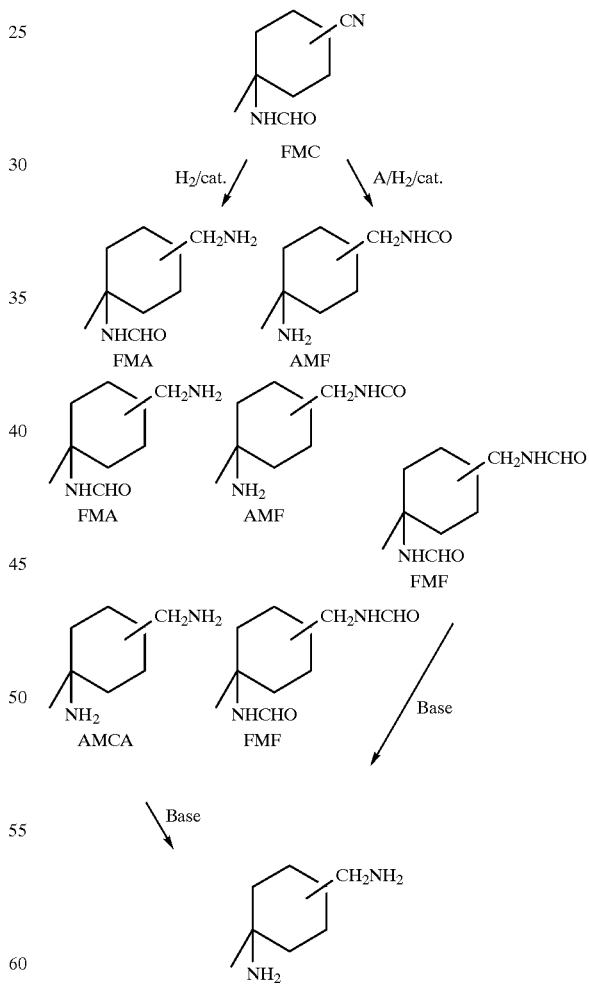

A: formylating reagent

The reaction products of the process according to the invention (AMCA, formic acid derivatives) are obtained in pure form by fractional distillation and/or by crystallization and filtration.

Suitable catalysts include Raney nickel, Raney cobalt and/or Raney iron catalysts, which are used as hydrogenation catalysts in an amount of 1 to 20 wt. %, based on the weight of FMC. Hydrogenation is carried out at temperatures of 50° C. to 200° C., preferably 60° C. to 160° C., and at a hydrogen pressure of 50 to 300 bar, preferably 70 to 200 bar.

The hydrogenation reaction may optionally take place in suitable solvents, such as hydroxyalkanes or alkylaromatics, preferably in solvents that are also suitable as extracting agents for FMC. The hydrogenation may be carried out either batchwise and continuously.

The alkaline compounds used for converting the formamido groups to amino group are preferably ammonia, alkali metal hydroxides and alkaline earth metal hydroxides.

The alkaline cleavage of the FMA, AMF and/or FMF obtained in the first reaction stage, which takes place with alkali metal hydroxides or alkaline earth metal hydroxides in the second reaction stage, is carried out at temperatures of 100° C. to 300° C., preferably 120° C. to 250° C. This reaction may be carried out in suitable solvents in which the resulting AMCA is soluble and the alkali metal formates or alkaline earth metal formates which are formed are insoluble. Suitable solvents include toluene and diphenyl ether. 1 to 2 moles of alkali metal hydroxides or 0.5 to 1 mole of alkaline earth metal hydroxides are used per mole of FMA and/or AMF. A 2 to 10 mole % excess of hydroxyl equivalents is preferably used. Preferred alkali metal hydroxides and alkaline earth metal hydroxides are sodium hydroxide, potassium hydroxide and calcium hydroxide.

The alkaline cleavage of the FMA, AMF and/or FMF obtained in the first reaction, which takes place with ammonia in the second reaction stage, is carried out at temperatures of 100° C. to 300° C., preferably 120° C. to 250° C. This reaction may be carried out in suitable solvents, such as hydroxyalkanes.

It is also possible to carry out the first and second reaction stages of the process according to the invention in a one-pot reaction. In this case the hydrogenation reaction is carried out in the presence of ammonia, alkali metal hydroxides and/or alkaline earth metal hydroxides, and unreacted FMA, AMF and/or FMF are returned after the separation of AMCA.

The hydrogenation of FMC may also take place in the presence of a formulating agent, wherein the bis-formamide, 1-formamido-1-methyl-3(4)-formamidomethyl cyclohexane (FMF), is formed as a new intermediate product. Formamide, alkyl formates and carbon monoxide may be used as the formulating agent. Methyl formate and carbon monoxide are preferred. The hydrogenation reaction may optionally take place in suitable solvents, such as hydroxyalkanes or alkylaromatics, preferably in solvents that are also suitable as extracting agents for FMC. The formulating agent may also serve as the solvent. The hydrogenation may be carried out either batchwise or continuously.

The alkaline cleavage of the bis-formamide (FMF) takes place as described previously for the cleavage of AMF, FMA and FMF. 2 to 3 mole of alkali metal hydroxide or 1 to 1.5 mole of alkaline earth metal hydroxide are used per mole of FMF. A 2 to 10 mole % excess of hydroxyl equivalents is preferably used. Preferred alkali metal hydroxides and alkaline earth metal hydroxides are sodium hydroxide, potassium hydroxide and calcium hydroxide.

The isolation of the starting material FMC from the reaction mixture of the Ritter reaction between CMC and hydrocyanic acid is known. It takes place by extraction from an aqueous acidic reaction mixture in which the sulphuric acid content has been adjusted, optionally by dilution with water, to approximately 10 to 70%, preferably 10 to 50%, after distilling off excess hydrocyanic acid.

When the FMC starting material is extracted from an acidic solution, it is possible, by concentrating the aqueous phase which remains, to recycle the sulphuric acid feedstock for the Ritter reaction.

Suitable solvents which may be used for the extraction include chlorinated hydrocarbons such as dichloromethane, chloroform and chlorobenzene; ethers such as t-butylmethyl ether or t-butyloxy-2-propanol; ketones such as methyl ethyl ketone; alcohols such as n-butanol, isobutanol, 1-pentanol, 2-methyl-1-butanol, 4-methyl-2-pentanol and cyclohexanol; and mixtures of these solvents.

After extraction the extracting agent may be separated from the FMC by distillation and recycled. The crude FMC obtained may be purified, optionally by distillation; however, it is preferred to supply the crude FMC directly to the subsequent hydrogenation. It is also possible to use in the subsequent hydrogenation stage the extract phase obtained in the FMC extraction, without distilling off the extracting agent, provided that solvents which are also suitable for the hydrogenation are used for the extraction.

Another embodiment known from the aforementioned German reference for isolating FMC from the aqueous reaction mixture obtained from the Ritter reaction involves neutralizing the acidic mixture with ammonia, optionally after dilution with water, such that the mixture contains 20 to 70 wt. % of ammonium sulphate, and then extracting with solvents the FMC which is present in the mixture. In this embodiment of isolating FMC a considerable quantity of ammonium salts is formed because of the neutralization of the sulphuric acid used in the Ritter reaction. However, this is an important process because the extraction is particularly complete even using small quantities of extracting agent, which reduces the energy requirement for further working up. The ammonium sulphate-containing effluent obtained in this variant of FMC isolation is distinguished by a low COD value, such that ammonium sulphate can be economically separated from it as a valuable by-product.

The AMCA obtained by the different embodiments of the process according to the invention may be phosgenated to IMCI in known manner.

All percentages in the examples are percentages by weight.

EXAMPLES

Example 1

363 g of 4(5)-cyano-1-methyl cyclohexene (isomer mixture obtained by the cyclo addition of isoprene and acrylonitrile) were incrementally added to a mixture of 5.4 moles of 88% sulphuric acid and 891 g of hydrocyanic acid at 27° C. to 29° C. over a period of 75 minutes, with stirring, wherein the heat of reaction was removed by refluxing the boiling hydrocyanic acid. Ten minutes after completion of the addition, 900 g of water were added and the excess hydrocyanic acid was distilled off. 735 g of a 25% aqueous ammonia solution were then added at 20° C. to 30° C. The neutralized reaction solution obtained was then extracted five times, in each case with 150 g of isobutanol. After removing the extracting agent, 525 g of crude 1-formamido-1-methyl-3(4)-cyano cyclohexane (isomer mixture) (88.5% yield, determined by gas chromatography) was obtained. The isobutanol dissolved in the aqueous ammonium sulphate solution obtained following extraction was removed by distillation. The aqueous ammonium sulphate solution (1800 g, sulphur content: 9.5%, corresponding to 39.5% ammonium sulphate), which remained and from which isobutanol had been removed, had a chemical oxygen demand (COD) of 3500 mg/l.

Comparative Example 1

175 g of crude 1-formamido-1-methyl-3(4)-cyano cyclohexane from Example 1 were dissolved in 476 g of 37% sulphuric acid and heated to 60° C. for 6 hours. The pH of the reaction solution was then adjusted to 1.8 by the addition of a 25% ammonia solution, and the formic acid contained in the reaction solution was removed by extraction with isobutanol. The aqueous phase obtained after formic acid extraction was adjusted to pH 10 by the addition of 25% ammonia solution and extracted six times, in each case with 300 g of isobutanol. After removal of the isobutanol, 157 g of crude 1-amino-1-methyl-3(4)-cyano cyclohexane (isomer mixture) were obtained (80.9% yield, determined by gas chromatography). The aqueous ammonium sulphate solution, which remained after removal of isobutanol and ammonia, was adjusted to a sulphur content of 9.5% and had a chemical oxygen demand (COD) of 10500 mg/l.

The Comparative Example shows that when 1-amino-1-methyl-3(4)-cyano cyclohexane (AMC) was isolated, an ammonium sulphate-containing effluent resulted which had a markedly higher COD value than when 1-formamido-1-methyl-3(4)-cyano cyclohexane (FMC) was isolated. In the case of the AMC isolation markedly higher costs were incurred in the further working-up of this effluent to obtain recyclable ammonium sulphate.

Example 2

175 g of crude 1-formamido-1-methyl-3(4)-cyano cyclohexane from Example 1 were dissolved in 400 g of methyl formate and hydrogenated with the addition of 9 g of Raney nickel at a hydrogen pressure of 150 bar and a temperature of 150° C. When the hydrogen uptake was complete, the catalyst was filtered, and excess methyl formate and methanol which had formed were distilled off. 210 g of crude 1-formamido-1-methyl-3(4)-formamidomethyl cyclohexane remained (83.3% yield, determined by gas chromatography).

Comparative Example 2

157 g of crude 1-amino-1-methyl-3(4)-cyano cyclohexane from Comparative Example 1 were hydrogenated in the presence of 200 g of methanol, 300 ml ammonia and 9 g of Raney nickel at a hydrogen pressure of 100 bar and a temperature of 100° C. to 120° C. After the hydrogen uptake was complete, the catalyst was filtered, and methanol and ammonia were removed by distillation. 146 g of crude 1-amino-1-methyl-3(4)-aminomethyl cyclohexane remained (73.4% yield, determined by gas chromatography). Approximately 20 wt. % was accounted for by the compounds of the formulas I, II, III, IV and V.

Example 3

210 g of crude 1-formamido-1-methyl-3(4)-formamidomethyl cyclohexane from Example 2 were heated in the presence of 300 g of toluene and 75 g of sodium hydroxide to 180° C. for six hours. After the sodium formate which formed was filtered and the toluene was distilled, a residue of 143 g of crude 1-amino-1-methyl-3(4)-aminomethyl cyclohexane remained (85.9% yield, determined by gas chromatography).

A total selectivity of 86.5% (based on the CMC feedstock) resulted from Examples 1 to 3 according to the invention. Conversely, the total selectivity for the process which proceeded via 1-amino-1-methyl-3(4)-cyano cyclohexane (AMC) was only 75.5% (see Comparative Examples 1 and 2).

Example 4

175 g of crude 1-formamido-1-methyl-3(4)-cyano cyclohexane from Example 1 were hydrogenated in 1.3 liters of methanol and 0.9 liters of ammonia with the addition of 9 g of Raney nickel at a hydrogen pressure of 100 bar and a temperature of 140° C. until the hydrogen uptake was complete. After the catalyst was filtered and methanol and ammonia were distilled, a residue of 180 g remained which contained 30% of 1-amino-1-methyl-3(4)-aminomethyl cyclohexane, 40% of 1-formamido-1-methyl-3(4)-aminomethyl cyclohexane and 1-amino-1-methyl-3(4)-formamidomethyl cyclohexane, and 13% of 1-formamido-1-methyl-3(4)-formamidomethyl cyclohexane (determined by gas chromatography).

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of 1-amino-1-methyl-3 (4)-aminomethyl cyclohexane (AMCA) which comprises a) catalytically hydrogenating 1-formamido-1-methyl-3 (4)-cyano cyclohexane (FMC) in a first reaction stage to form 1-formamido-1-methyl-3(4)-aminomethyl cyclohexane (FMA), 1-amino-1-methyl-3(4)-formamidomethyl cyclohexane (AMF), 1-formamido-1-methyl-3(4)-formamidomethyl cyclohexane (FMF) and/or AMCA, and b) reacting FMA, AMF and/or FMF in a second reaction stage with an alkaline compound to form AMCA and a formic acid derivative, and c) separating the reaction mixture obtained in step b) into components by fractional distillation and/or by crystallization and filtration.

2. The process of claim 1 wherein the hydrogenation catalyst comprises a Raney nickel, Raney cobalt and/or Raney iron catalyst.

3. The process of claim 1, characterized in that the hydrogenation is carried out in a solvent.

4. The process of claim 1 which comprises using ammonia as said alkaline compound, separating the resulting AMCA and formamide by fractional distillation, and optionally recycling unreacted FMA, AMF and/or FMF to the reaction stage.

5. The process of claim 1 which comprises using an alkali metal hydroxide and/or an alkaline earth metal hydroxide as said alkaline compound, separating the resulting AMCE and formate salt by crystallization, filtration and distillation, and optionally recycling unreacted FMA, AMF and/or FMF to the reaction stage.

6. The process of claim 5 wherein step b) is carried out in a solvent in which the AMCA is soluble and the formate salt is insoluble.

7. The process of claim 1 wherein step a) is carried out in the presence of a formulating agent to form 1-formamido-1-methyl-3(4)-formamidomethyl cyclohexane (FMF).

8. The process of claim 7 wherein the formulating agent comprises formamide, a formic acid ester or carbon monoxide.

9. The process of claim 1 wherein steps a) and b) are carried out in one reaction vessel.

10. 1-Formamido-1-methyl-3(4)-aminomethyl cyclohexane.

11. 1-Formamido-1-methyl-3(4)-formamidomethyl cyclohexane.

* * * * *